(12) United States Patent
Knappe

(10) Patent No.: US 7,347,971 B2
(45) Date of Patent: *Mar. 25, 2008

(54) SPREADING LAYERS AND THEIR USE IN TEST STRIPS

(75) Inventor: Wolfgang-Reinhold Knappe, Ludwigshafen (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/426,931

(22) Filed: Oct. 22, 1999

(65) Prior Publication Data

US 2003/0031592 A1 Feb. 13, 2003

(30) Foreign Application Priority Data

Oct. 23, 1998 (DE) ............... 198 49 008

(51) Int. Cl.
*G01N 33/48* (2006.01)

(52) U.S. Cl. ............... 422/58; 422/57; 422/61

(58) Field of Classification Search ............ 422/56, 422/57, 58, 61
See application file for complete search history.

(56) References Cited

U.S. PATENT DOCUMENTS

| | | | |
|---|---|---|---|
| 3,762,875 A | 10/1973 | Burmeister | |
| 3,802,842 A | 4/1974 | Lange et al. | 23/253 TP |
| 4,046,514 A | 9/1977 | Johnston et al. | 23/253 TP |
| 4,220,713 A | 9/1980 | Rittersdorf et al. | 435/14 |
| 4,312,834 A | 1/1982 | Vogel et al. | 422/56 |
| 4,370,412 A | 1/1983 | Cruikshank et al. | 430/635 |
| 4,385,114 A | 5/1983 | Guthlein et al. | 435/281 |
| 4,732,849 A | 3/1988 | Seshimoto et al. | 435/12 |
| 5,536,470 A | 7/1996 | Frey et al. | 422/56 |
| 5,695,947 A | 12/1997 | Guo et al. | 435/11 |
| 5,779,867 A | 7/1998 | Shieh | 204/403 |
| 5,846,837 A | 12/1998 | Thym et al. | 436/170 |
| 6,025,203 A * | 2/2000 | Vetter et al. | 436/170 |
| 6,055,060 A | 4/2000 | Bolduan et al. | 356/433 |
| 6,194,224 B1* | 2/2001 | Good et al. | 436/518 |
| 6,241,689 B1* | 6/2001 | Chard et al. | 600/584 |
| 6,455,001 B1* | 9/2002 | Knappe et al. | 422/56 |
| 6,537,496 B1* | 3/2003 | Knappe et al. | 422/58 |

FOREIGN PATENT DOCUMENTS

| | | |
|---|---|---|
| AU | 702209 | 1/1998 |
| DE | 2118455 | 9/1972 |
| DE | 2752352 A1 | 6/1978 |
| DE | 2729283 A1 | 2/1979 |
| DE | 3042857 A1 | 5/1981 |
| EP | 0016387 B1 | 10/1980 |
| EP | 0 109 012 | 5/1984 |
| EP | 0109012 A2 | 5/1984 |
| EP | 0819943 A2 | 1/1998 |
| EP | 0821233 A2 | 1/1998 |
| EP | 0 985 930 | 3/2000 |
| WO | WO92/15879 | 9/1992 |
| WO | WO 97/18036 | 5/1997 |
| WO | WO97/18036 | 5/1997 |
| WO | WO00/07016 | 2/2000 |

* cited by examiner

*Primary Examiner*—Lyle A. Alexander
(74) *Attorney, Agent, or Firm*—Woodard, Emhardt, Moriarty, McNett & Henry LLP

(57) ABSTRACT

A spreading material is described which comprises a porous flat-shaped structure impregnated with a wetting agent, wherein the wetting agent is N-oleoyl-sarcosinate.

4 Claims, 2 Drawing Sheets

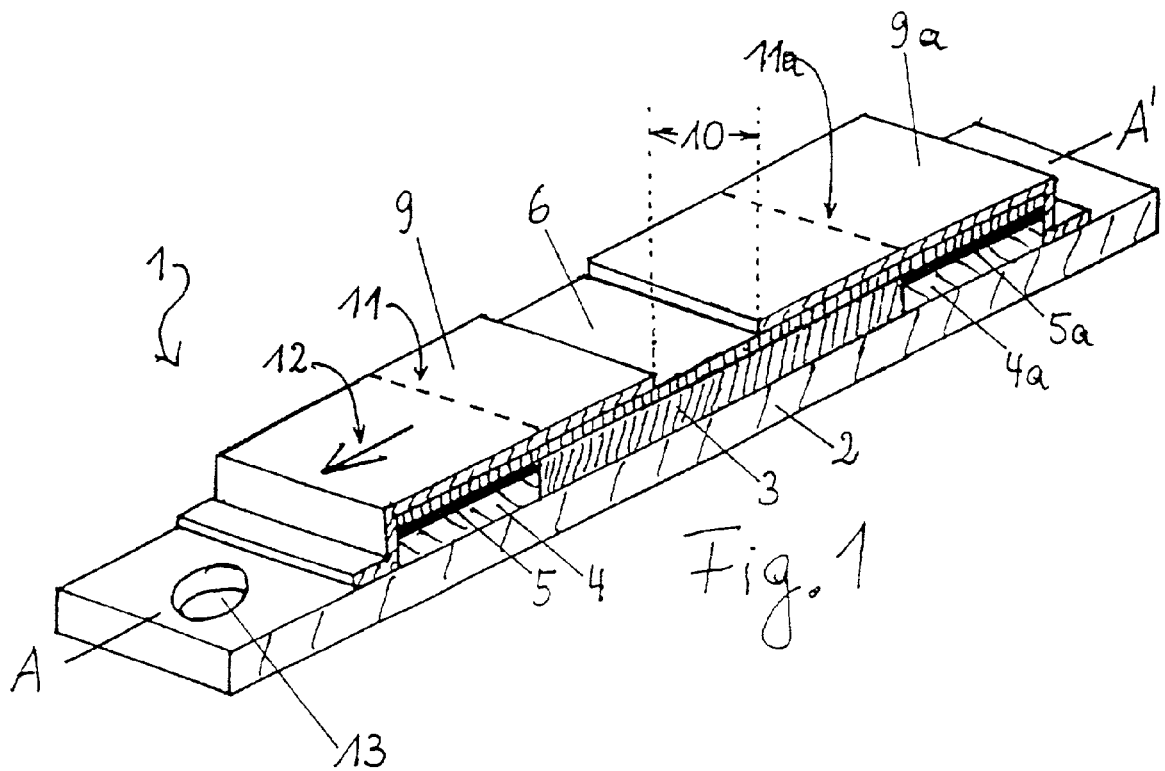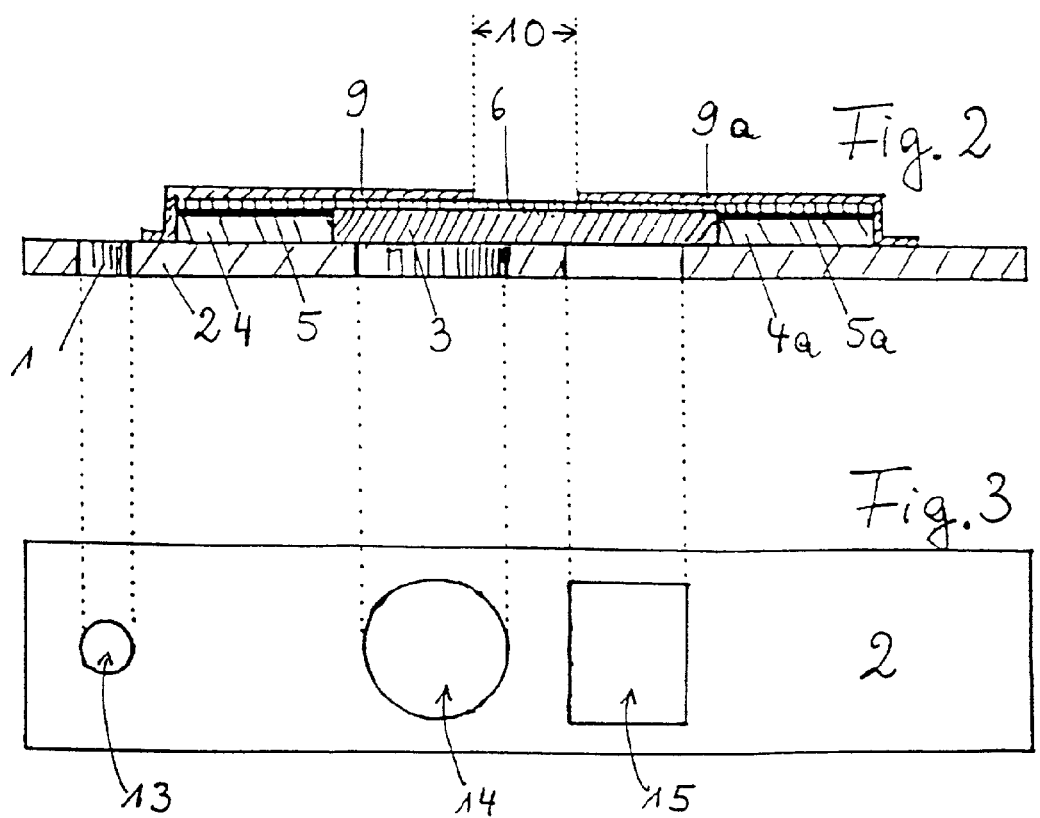

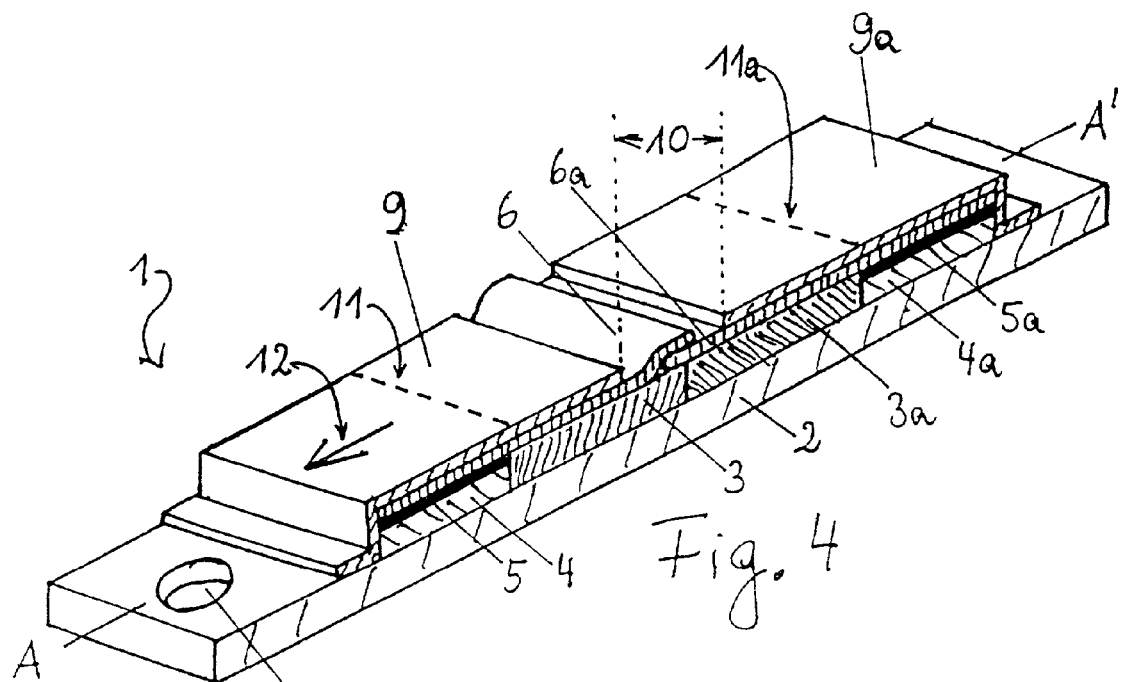
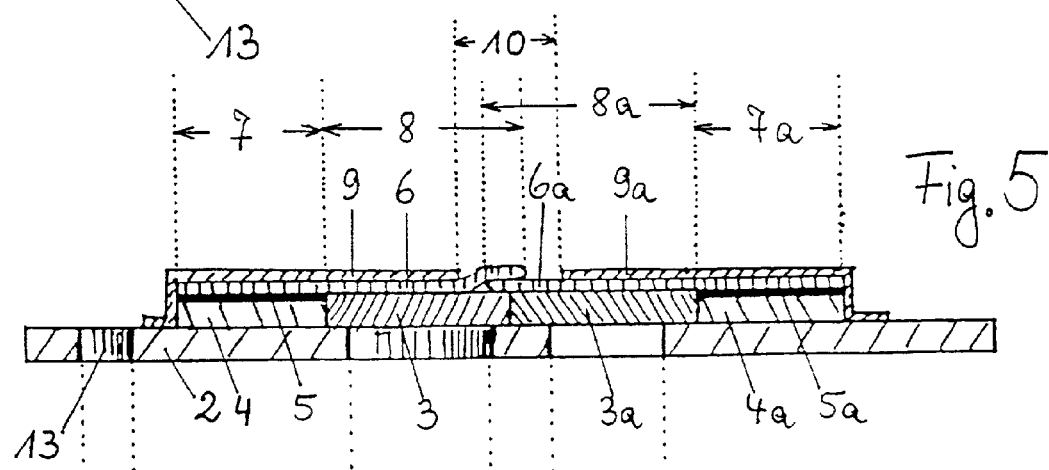
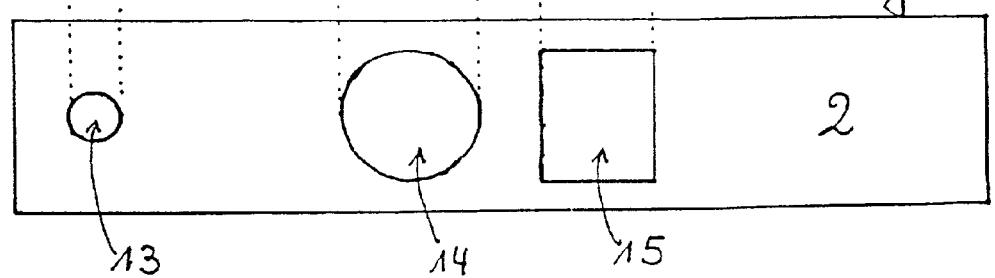

SPREADING LAYERS AND THEIR USE IN TEST STRIPS

The present invention concerns spreading layers comprising a porous flat-shaped structure impregnated with N-acyl-N-alkyl-glycinates, the production of this spreading material using N-acyl-N-alkyl-glycinates and test strips which contain the spreading material according to the invention.

So-called carrier-bound tests are often used for the qualitative or quantitative analytical determination of components of body fluids in particular of blood. In these the reagents are present on or in corresponding layers of a solid test carrier which is contacted with the sample. The reaction of liquid sample and reagents leads to a detectable signal especially to a change in colour which can be evaluated visually or with the aid of an instrument, usually by reflection photometry.

Test carriers are frequently in the form of test strips which are essentially composed of an oblong support layer made of plastic material and detection layers mounted thereon as test fields. However, test carriers are also known which are designed as small quadratic or rectangular plates. In the following description the term "test strips" is also intended to encompass test carriers which do not have a strip shape.

Test carriers of the above-mentioned type are for example known from the German Patent document 21 18 455. This describes diagnostic test carriers for the detection of analytes in liquids which are composed of a support layer and at least one detection layer containing the detection reagents which is provided with a cover layer on its surface that does not adjoin the support layer. The cover layer can be composed of a fine-meshed network in the form of a fabric, knitted fabric or fleece. Plastic fabrics are stated as preferred networks in order to achieve a rapid wetting of the detection layer with sample liquid and to avoid interfering chromatographic effects. In order to detect an analyte in a liquid, such a diagnostic test carrier is dipped into a corresponding liquid preferably urine. In this manner the detection layer comes into contact with a very large excess of liquid which cannot be taken up by the test carrier. However, depending on the duration of contact of the detection layer with the liquid to be examined different colour intensities can be observed.

As a rule the results obtained are more positive the longer the contact time is. Therefore a correct quantitative analyte determination is not possible in this manner when there is a large excess of sample.

On the other hand a sample volume that is too small for a test carrier construction is a frequent cause for false measured values in diabetes monitoring i.e. the regular control of the blood of diabetics for the content of glucose.

Test carriers with the smallest possible volume requirement are therefore the goal of diverse current developments.

Test strips are known from DE-A-3042857 which have a sample distribution layer (spreading layer) on their multi-layer analytical elements which has the function of uniformly distributing sample liquid applied as a spot over the entire test element. This spreading layer is composed of a cloth or a foam layer which is hydrophilized by impregnation with a wetting agent and is either pressed onto the still wet uppermost gelatine layer of the analytical element or is attached thereto by means of an additional adhesive layer.

In the practical examples of this document a cotton fabric or a filter cloth are used as a spreading layer and the non-ionic wetting agent polyoxyethylene nonylphenoxy ether is used for hydrophilization.

Diagnostic test carriers in the form of test strips which offer a considerable advance with regard to reproducibility of the test results even when different sample volumes are applied and with regard to hygienic handling are known from EP-A-0 821 233.

They contain a support layer with a detection layer arranged thereon containing reagents required to determine the analyte in a liquid sample and an overlay made of a network covering the detection layer which is larger than the detection layer and is attached to the support layer on both sides of the detection layer preferably via a spacer and in contrast rests directly on the detection layer without attachment i.e. essentially is in contact with the whole surface of this without a gap. The network used as an overlay should be hydrophilic but not alone be capillary active. Also in this case the network is impregnated with a wetting agent for hydrophilization namely sodium dioctylsulfosuccinate.

In this construction the network covering the detection layer is preferably composed of high denier, relatively coarse-meshed monofilament fabric with an adequately large mesh size so that liquid can pass through the net onto the detection layer (page 3, line 2). In the example of this application a monofilament fabric with a mesh size of 280 µm is used. It has an important function: it rapidly passes sample liquid applied to its surface onto the underlying detection layer. When the detection layer is saturated a sample excess which may be present is led away into the boundary regions of the network which extend beyond the detection layer. In this manner small amounts of sample are made completely available to the detection layer but longer exposure to a ample excess which can lead to false-positive results is avoided.

An embodiment is also described in this document which has two or several detection layers arranged next to one another which are intended for the measurement of the same or different analytes.

The use of test carriers of this design of course at first sight offers tempting advantages with regard to work and cost savings since it should enable two or even several measurements to be carried out with a single application of sample. However, in practice when it is attempted to use this embodiment difficulties arise which are due to the fact that the spreading action of the relatively coarse meshed network is not sufficient in multifield test strip constructions to distribute the analyte samples over both detection fields. Only when the analyte sample is very carefully applied accurately over the border between both test fields, which can be seldom achieved in practice, is it possible to wet both test fields, but then a minimum sample volume of over 15 µl is required to completely wet the test fields.

Even the attempt to wet both test fields by placing the fields directly next to one another on the support without a gap does not lead to success. It turns out that even the tiny distance between the test fields of 5 to 10 µm which is still present in this case prevents blood from "jumping" from one to the other field.

Hence although there are attempts to further improve and to economise the analytical methods using test strips there are, however, still considerable obstacles to their practical application.

There is a lack of technical teaching to enable analyte samples to be distributed rapidly and uniformly over an arrangement of test fields especially when small sample volumes are available and/or several test fields are arranged next to one another. Thus for the quantitative detection of analytes such as glucose in capillary blood there is among others a need to uniformly distribute about 3 µl blood in less than 2 seconds over the relatively large area of 30 mm$^2$ in the case of a single field test. In the case of a two field test, it is necessary to even distribute 5 µl blood over two test fields each of ca. 30 mm².

Also the time factor is of major significance in such methods: It is not at all only a question of accelerating the test procedure but rather it is important to uniformly distribute the analyte with as little delay as possible in the entire test layer since, as already stated above, a time delay can result in a gradient of the analytical result over the test field thus burdening the determination with a considerable uncertainty factor.

To the knowledge of the patent applicant the problems resulting from these requirements have not yet been satisfactorily solved in a simple manner.

It was now surprisingly found that the sample volume required for the measurement can be reduced to ca. 4 µl and a very uniform distribution of the sample even over several adjacent detection fields can be achieved in a time of less than 2 seconds if the detection fields are covered with the spreading material accÀrding to the invention which is described in the following.

The spreading material according to the invention comprises a porous sheet structure impregnated with a wetting agent which is characterized in that the wetting agent is an N-acyl-N-alkyl-glycinate of formula I

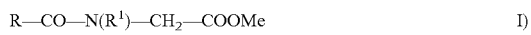

R—CO—N(R¹)—CH₂—COOMe        I)

in which R denotes an aliphatic residue with 9 to 23 C atoms, in particular 11 to 17 C atoms, which is saturated and has one to three double bonds, R¹ denotes hydrogen or lower alkyl and Me is hydrogen or a metal atom.

R is in particular the aliphatic chain of lauric acid, myristic acid, palmitic acid, stearic acid or palmitoleic acid, oleic acid (olein), linoleic acid, linolenic acid and isomers thereof.

The use of an N-acyl-N-alkylglycinate mixture is also very advantageous in which the structure and proportion in the mixture of the residues R corresponds to the structure and abundance of alkyl residues of natural fatty acids, e.g. tallow fat or coconut fatty acid In technical usage such alkyl mixtures are for example referred to as "tallow fatty alkyl" or "coconut fatty alkyl".

Lower alkyl groups representing R¹ are preferably linear and have 1 to 4, in particular 1 or 2 C atoms. A methyl group is particularly preferred for R¹.

The metal atom Me is expediently selected such that the glycinate of formula I is water-soluble. In particular alkali metals, preferably sodium and potassium, are suitable. A spreading material according to the invention which is impregnated with sodium N-oleoyl-sarcosinate is particularly preferred. Sodium N-oleoyl-sarcosinate can be readily prepared by reacting N-oleoyl-sarcosine (e.g. the commercial product Crodasinic® O from the Croda Company, Nettetal, Germany) with an equivalent amount of sodium hydroxide solution.

In connection with the material description of the spreading material according to the invention the feature "impregnated" means that the material carries a coating of the impregnating agent on its surface which is accessible to liquids i.e. pores and spaces between filaments are also "lined" with this agent. The coating of the compound according to the invention hydrophilizes the porous sheet structure particularly advantageously which is why it is particularly suitable as a spreading material.

By nature the local surface concentration of the impregnating agent depends on the accessibility of the respective surface element. This is, however, of secondary importance for the hydrophilizing effect of the surface coating.

In order to achieve a hydrophilically active coating on overlay materials according to the invention an amount of 0.01 to 2% by weight, preferably of 0.03 to 0.5% by weight, of the glycinate relative to the weight of the overlay material before impregnation is usually adequate.

The superior spreading action of the spreading material according to the invention is closely linked to the presence of a wetting agent of formula I in the material. The superiority of the wetting agent of formula I used according to the invention compared to that used in the nearest comparable prior art EP-A-0 821 233 can be demonstrated by a simple experiment:

A fleece material (Viledon® FO 2451/121 from the Freudenberg Company, Weinheim, Germany) is impregnated in a 0.5% by weight aqueous solution of sodium dioctyl-sulfosuccinate (the wetting agent used in EP-A-0 821 233) until saturation and dried in the air. A blood sample of 5 to 10 µl is placed on a ca. 3×3 cm horizontally clamped piece of the fleece material impregnated in this manner. The blood remains as a hemisphere on the upper side of the fleece material, the underside does not become wet.

If the same amount of blood is applied to a piece of the fleece material impregnated with sodium dioctyl-sulfosuccinate which rests on a reagent film then the drop of blood also stands on the upperside of the fleece without wetting the film and hence no reaction occurs. Blood does not reach the underside of the fleece and spreading and reaction do not occur until the blood is mechanically pressed through at one position e.g. by touching the fleece with a pipette tip.

If the described experiment is repeated in exactly the same manner with the only difference being that an aqueous 0.1% by weight solution of sodium N-oleoyl-sarcosinate is used instead of the sodium dioctyl-sulfosuccinate solution to impregnate the fleece material, then the applied blood penetrates the fleece and hangs as a semicircle from the underside. If the fleece rests on a reagent film when the blood is applied, the blood reaches spontaneously the underside and spreading and reaction occur.

The demonstrated superiority of the compounds of formula I when used as spreading agents is very surprising. A large number of wetting agents are known from a variety of groups of chemical compounds. A common feature is that they have a hydrophilic and a hydrophobic part of the molecule.

Wetting agents with non-ionic, anionic, cationic and amphoteric properties are described in Ullmanns Encyclopedia of Technical Chemistry, vol.5. On page 778 succinic acid derivatives and in particular sulfosuccinic acid dialkyl esters from the group of anionic wetting agents are emphasized as wetting agents with an outstanding effectiveness which are used for an extremely wide range of technical applications.

On page 751 of this standard work derivatives of aminocarboxylic acids including amino-acetic acid which is also a structural element of the compounds of formula I according to the invention are mentioned as wetting agents and allocated to the group of amphoteric wetting agents. In this connection it is stated on pages 795/796 that these have only gained minor technical significance especially due to the strong dependence of their properties on the pH value.

It was therefore not predictable that compounds of formula I when used as spreading agents would be considerably superior to the sulfosuccinic acid esters known as excellent wetting agents.

The porous flat-shaped structure which is the basis of the spreading material according to the invention is a textile fabric made of monofilaments or corresponding multifilament yarns which is itself not capillary active but permeable to liquids and its construction and material and/or hydrophilizing finish are selected such that it spreads 10 µl of water over an area of more than 300 mm² when resting on a support.

Textile fabrics which fulfil this requirement may be found among commercial materials. Suitable textile materials can be basically initially selected according to the motto "as thin as possible with a weight per unit area which is as small as possible". The following spreading test can be used for the fine selection of suitable materials.

10 mm wide and at least 100 mm long strips of the textile material to be examined which may optionally have a hydrophilic finish are placed on the matted side of a polycarbonate foil. Then 10 µl water is applied as a spot to the middle of the strip and its spreading is observed. With a suitable material the spreading process should be completed within 5 to 10 seconds and the wetted area should be at least 30×10 mm.

This test can for example be used to demonstrate the major differences between the polyester fabric PE 280 HC used according to EP-A-0 821 233 as a spreading material and the textile materials used according to the invention e.g. the polyester fabric PE 38 HC or Viledon fleece material FO 2451/121 as follows:

10 mm wide strips of the textile materials to be tested are impregnated with the same coating (ca. 0.25% by weight relative to the material weight before impregnation) of sodium-N-oleoyl sarcosinate and dried. Then the impregnated textile strips are placed on the matted side of a polycarbonate foil. If 10 µl water is then applied as a spot, the water spreads in 5 to 10 seconds over the areas stated in the following table and then comes to a standstill:

| According to | Material | Area |
|---|---|---|
| EP-A-0821233 | PE 280 HC | 8 × 10 mm |
| invention | PE 38 HC | 40 × 10 mm |
| invention | Viledon FO 2451/121 | 50 × 10 mm |

Fabrics, knitted fabrics or fleeces with a thickness of 20 to 200 µm, preferably of 30 to 100 µm and/or a pore volume of 30 to 85, preferably of 40 to 75% have proven to be particularly suitable as textile materials for spreading small□amounts of blood. The weight per unit area of these particularly suitable materials for spreading small sample volumes is 10 to 200, preferably 10 to 50 g/m².

In this connection materials with thicknesses below 100 µm in particular below 50 µm and weights per unit area of below 50 and preferably below 25 g/m² are particularly preferred.

Particularly preferred flat-shaped structures with the said dimensions are fabrics and fleeces. Preferred fabrics are those which have a mesh size below 200 µm, preferably of 20 to 150 µm in particular of 20 to 60 µm, are slip-resistant and are manufactured from monofilaments with deniers in the range of 2 to 20 dtex, preferably 4 to 15 dtex in a linen weave. The fabrics can also have a slip-resistant finish applied after weaving. However, the slip-resistance of the fabric is preferably achieved by impressing a wave-like deformation on the monofilaments during the fabric manufacture and/or by slightly melting together the warp and weft filaments at the crossing points which secures them against slipping.

Fleeces used according to the invention are random fleeces preferably spun-bonded fleeces. They are composed of continuous monofilaments with a denier in the range of 0.5 to 2.5 dtex, preferably of 0.8 to 2.0 dtex. The bonding can be carried out by treating the fleeces with bonding agents; however, autogenic bonding is preferred in which the filaments are gently melted together at their crossing points. The pores of such fleeces inherently have considerable size differences. Surprisingly fleeces with the features stated above are outstandingly suitable for the inventive use despite the large variation in pore size.

The slight or absent capillary activity of the flat-shaped structure is exhibited by the fact that it has a height of rise of water at 25° C. of less than 2 mm in 10 sec.

Fibre materials that come into consideration for the textile materials to be used according to the invention are natural fibres such as cellulose or protein fibres, semisynthetic fibres such as acetate or viscose silk or completely synthetic fibres such as polyester, polyamide, polyurethane or polyacrylonitrile, poly-ethylene or polypropylene fibres or mixtures of the said fibre types.

Preferred cellulose fibres are cotton fibres, preferred protein fibres are wool and natural silk. Suitable acetate fibres are 2,5- or triacetate fibres depending on the desired degree of hydrophilicity. Preferred synthetic fibres are composed of polyethylene terephthalate, polyamide-6, polyamide-6,6 or modified polyacrylonitrile.

Synthetic and in particular thermoplastic fibres are preferred over natural fibres due to their high resistance to environmental influences and the possibility of modifying mechanical and chemical properties according to need during their manufacture.

Commercial textile flat-shaped structures which can be used according to the invention especially after a hydrophilization are for example the monofilament polyester fabric type PE nn HC or the monofilament nylon fabric type NY nn HC or HD from the ZBF Mesh+Technology Company, Ruschlikon, Switzerland in which nn varies from 20 to 150, in particular the polyester fabric type PE 38 HC or the monofilament nylon fabric type NY 41 HC. The Viledon® fleece materials FO 2451, in particular type FO 2451/121 from the Freudenberg Company, Weinheim, Germany are very well suited for use according to the invention.

The use of the spreading material according to the invention is of course not limited to an application in the construction of test strips although it is of special importance in the construction of diagnostic test strips. On the contrary the spreading material according to the invention can be used in any technical applications where a rapid and uniform distribution of liquids over relatively large areas is important such as e.g. in the development of extremely large size silver halogenide pictures with a limited amount of developer and for certain tone separation processes in artistic photography.

A subject matter of the present invention is also the use of compounds of formula I in which the residues R, R¹ and Me have the above-mentioned meanings for the production of a spreading material.

Compounds of formula I can be used to produce the spreading material in a pure form or in the form of preparations and especially in the form of solutions or liquid preparations.

A preparation can be composed of a solution or finely divided dispersion of one or several compounds of formula I in water, in an inert organic solvent or in a solvent/water mixture. It can also be an emulsion of an aqueous solution of compounds of formula in a solvent that is immiscible with water.

In addition to the compounds of formula I the formulations can also contain other additives and/or auxiliary substances which either interact synergistically with these or which for example act as impregnation adjuvants, as stabilizers or as protective colloids. Furthermore in addition to the compounds of formula I the formulations can contain substances which impart additional functions or other advantageous properties to the spreading material. Thus the formulations can for example also contain finely dispersed inorganic or organic filter materials or fillers. Also dyes which impart a recognition colour to the spreading material or which are suitable for improving the detectability of the colour reaction of the detection layers or the complete wetting of the spreading material, or absorb UV radiation are examples of additives which can be present in the formulations of the compounds of formula I used according to the invention.

The invention also concerns a process for the production of a spreading material by impregnation of a porous flat-shaped material with a wetting agent or a wetting agent formulation, optionally adjusting the impregnated flat-shaped material to a predetermined wetting agent uptake and optionally drying the material, which is characterized in that at least one compound of formula I in which the symbols R, $R^1$ and Me have the above-mentioned meanings is used.

Wetting agent formulations to be used in the process according to the invention have already been described.

All methods which lead to a statistically uniform distribution of the wetting agent of formula I in the porous flat-shaped material are suitable for the impregnation. Usually the wetting agent is applied in the form of a solution or a liquid formulation.

The impregnating agent expediently contains 0.01 to 2% by weight, preferably 0.03 to 1% by weight and in particular 0.07 to 0.3% by weight of the wetting agent of formula I.

It can be applied in any conventional manner for example by immersion, spraying or by brush coating. It is also possible to powder the porous materials with a fine powder of compounds of formula I or solid formulations of the same.

Compounds of formula I are preferably applied in the form of aqueous solutions.

The applied amount of compounds of formula I or of the corresponding formulations is such that a coating of 0.01 to 2.0% by weight, preferably 0.03 to 0.5% by weight N-acyl-N-alkyl-glycinate of formula I relative to the weight of the material before impregnation remains on the porous material or an applied excess is removed to achieve the same.

Since the wetting agent of formula I is usually applied in the form of solutions or liquid formulations, it is necessary to dry the impregnated material after impregnation. This can take place in any suitable manner for textile materials or open pored foam materials. Usually the material is dried at temperatures between 10° C. and the boiling point of the liquid phase contained in the application agent, preferably at 20 to 80° C. The drying process can be facilitated by a vacuum and/or air circulation. Heat can be supplied by convection using a heat carrier, by contact with heating elements or by radiation. It is expedient to dry the flat-shaped material in a spread out state.

In addition to the spreading material according to the invention, a test strip is also a subject matter of the present invention composed of a flexible flat-shaped support on which one or several test fields are arranged next to one another which each carry one or several detection layers stacked on top of one another which is characterized in that the test fields are covered by a spreading material according to the invention described above.

Test strips according to the invention should preferably be used for diagnostic purposes. Test strips which are especially preferred have two directly adjacent single or multilayer test fields for the same or different analytes whereby in practice a microscopic gap of ca. 5-10 μm is also present in this case. It is also possible to accommodate more than two test fields on a test strip.

The detection layers applied to the test fields contain reagents for the detection of a diagnostically utilizable analyte. The detection of the same analyte on two separate test fields may be of interest when the purpose of the detection layers is to enable a qualitative, semi-quantitative or quantitative assessment of very different concentrations of the analyte or if simply an assessment of the reproducibility of the measured result is desired. Of course the case is of particular interest where both detection layers enable the simultaneous qualitative detection or a semiquantitative or quantitative determination of two different analytes and especially those which are of diagnostic interest.

The spreading material is not attached to the detection field or detection fields but only rests loosely on them. In contrast to the teaching known from DE-A-30 42 857 (page 10) for the manufacture of test strips they are not pressed into the detection layers or glued thereto. Such a permanent connection would make the described spreading function impossible.

The spreading material is only attached to the test strip on both sides of the test field or the test fields preferably on spacers provided with adhesion layers. However, in this type of attachment the spreading material can form a fold over the test field in unfavourable cases if the test strip which is usually flexible is subjected to bending during use. The wrinkling impairs the distribution of the reagent sample over the test field. This wrinkling can be avoided when the overlay of the spreading material according to the invention is composed of one or several flat-shaped overlay elements which are attached to the flexible test strip in such a way that at least a part of their surface can move freely relative to the surface of the object covered by this part in the direction of curvature produced when the object is bent. This preferred manner of attaching an overlay element of the overlay according to the invention to the flexible object is carried out by using at least one, preferably at least two, attachment points which are in a connected surface area (attachment region) of the overlay element which extends between the edges of the overlay element lying in the direction of curvature and whose boundary to the freely movable part of the overlay element is essentially a straight line and at right angles to the direction of curvature.

If the test strip has two test fields they can be covered by a spreading overlay according to the invention of the type described above in a particularly practical manner in that the test fields are covered by two overlay elements which are attached to the test strip in such a way that their movable regions face one another and overlap.

In this case an optimal distribution of the sample is achieved if the two overlay elements overlap over the separation line between the two test fields and this overlap is preferably symmetrical thereto.

The inventive type of attachment which avoids wrinkling when the test strip is bent makes a very valuable contribution to reliable use especially for test strips whose correct function is particularly important and must be ensured under various conditions of use and when used by laymen with various degrees of skill.

The test fields are preferably mounted on the test carrier one behind the other in the direction of its longitudinal axis and the spreading overlay elements, viewed in the same direction, are attached in a zone on the flexible support which is located in front of and behind the test fields.

In addition it is preferred that the spreading overlay elements are attached to spacers which have approximately the thickness of the detection layers.

Finally it has proven to be expedient when the arrangement of detection layers and overlays on the test strip is covered with an inert flat-shaped material in such a manner that, viewed in the direction of the longitudinal axis of the test strip, a space only remains free that is adequate for sample application in the region where the overlay elements overlap which is usually 2 to 5 mm.

The support of the test strip is composed of a transparent material and/or has cut-outs in the region of the test fields of the same or different shape through which the underside of the detection layers can be inspected. It is advantageous especially for an automation of the test evaluation when the support of the test strip has adjustment marks in the form of additional holes, cut-outs or notches.

BRIEF DESCRIPTION OF THE DRAWINGS

FIGS. 1 to 6 serve to illustrate the abovementioned and the following description.

FIG. 1 shows a perspective top-view,

FIG. 2 shows a section along the cut line A-A',

FIG. 3 shows a top-view of the underside of an embodiment of a test strip according to the invention.

FIG. 4 shows a perspective top-view,

FIG. 5 shows a section along the cut line A-A',

FIG. 6 shows a top-view of the underside of an embodiment of a test strip according to the invention in which the spreading overlay according to the invention is composed of two overlay elements which are attached to the test strip in a preferred manner.

The reference numerals used in the figures have the following meaning:

| | |
|---|---|
| 1: | test strip |
| 2: | flexible carrier |
| 3 and 3a: | detection layers |
| 4 and 4a: | spacers |
| 5 and 5a: | adhesion layers |
| 6: | overlay according to the invention |
| 6 and 6a: | overlay elements according to the invention |
| 7 and 7a: | attachment region |
| 8 and 8a: | movable region |
| 9 and 9a: | protective cover |
| 10: | application area |
| 11 and 11a: | mark for the borders of the detection fields |
| 12: | mark for the direction of insertion |
| 13: | positioning hole |
| 14 and 15: | observation and measurement openings |

FIG. 1 shows a perspective top-view, FIG. 2 shows a section along the cut line A-A' in FIG. 1, FIG. 3 shows a top-view of the underside of an embodiment of a test strip according to the invention with a detection area and a spreading overlay according to the invention. This diagram is not to scale in order to clearly illustrate the construction. A concrete dimensioning of this embodiment can be seen in the practical example 1.

The diagnostic test strip (1) according to the invention shown perspectively in FIG. 1, in section in FIG. 2 and from below in FIG. 3 has a detection layer (3) on a support layer (2) which is covered by the spreading layer (6). The spreading layer (6) is attached to the support layer (2) next to the detection layer (3) by means of spacers (4, 4a) and adhesion layers (5, 5a). These spacers can in practice also be hot-melt adhesive areas or double-sided adhesive tapes which fix the spreading overlay (6) on the support layer (2). Ideally the spacers together with their adhesive surfaces have approximately the same thickness as the detection layer (3). The construction shown here additionally has covers (9, 9a) which are attached to the support layer (2) and to the spreading overlay (6). They are arranged in such a way that they cover the regions extending beyond the detection layer (3) and a part of the area of the spreading overlay (6) resting on the detection layer. However, they leave an area in the middle of the detection layer free which represents the sample application site (10). The sample liquid to be examined is applied to this. The left cover (9) contains a printed arrow (12) which shows the user which end of the test carrier (1) he should place or insert into a measuring instrument. The positioning hole (13) serves to hold the test strip, in the case of a measurement by an apparatus such as by reflection photometry, at an exactly predetermined position of the apparatus. This can for example be achieved in that for example a pin extends into the positioning hole (13) and in this manner fixes the test carrier (1) at a predetermined position.

FIG. 3 shows the underside of the test strip according to the invention containing the positioning hole (13) placed in the support (2) and the round observation opening (14) through which the detection layer can be inspected and measured.

FIG. 4 shows a perspective top-view, FIG. 5 shows a section along the cut line A-A in FIG. 4, FIG. 6 shows a top-view of the underside of an embodiment of a test strip according to the invention with two directly adjacent detection areas and a spreading overlay according to the invention which is fixed over the detection layers in the particularly preferred type of one-sided attachment described above. This representation is also not to scale in order to make the construction clearly visible. A concrete dimensioning of this embodiment can be derived from the practical example 2.

The diagnostic test strip (1) according to the invention shown perspectively in FIG. 4, in section in FIG. 5 and from below in FIG. 6 has two directly adjacent detection layers (3, 3a) on a support layer (2) which are covered by the spreading overlay elements (6, 6a). The overlay elements (6, 6a) are attached to the support layer (2) next to the detection layers (3, 3a) by means of spacers (4, 4a) and adhesion layers (5, 5a). These spacers can in practice also be hot-melt adhesive areas or double-sided adhesive tapes which fix the spreading overlay elements (6, 6a) on the support layer (2). Ideally the spacers together with their adhesive surfaces have approximately the same thickness as the detection layers (3, 3a). The construction shown here additionally has covers (9, 9a) which are attached to the support layer (2) and to the spreading overlays (6, 6a). They are arranged in such a way that they cover the regions extending beyond the detection layers (3, 3a) and a part of the area of the overlays (6, 6a) resting on the detection layer. However, they only leave the overlapping region of the overlay elements (6, 6a)

located above the border of the detection fields free. This region is the sample application site (10). The sample liquid to be examined is applied to this. If the covers are transparent, markings (11, 11*a*) may be applied to them over the external limits of the detection fields which enable the user to recognize whether the overlays have completely saturated detection fields with sample liquid. If this is the case then the sample quantity was adequate, otherwise it may be suspected that the amount of sample was too small and that possibly the measurement is erroneous. The left cover (9) contains a printed arrow (12) which shows the user which end of the test carrier (1) he should place or insert into a measuring instrument. The positioning hole (13) serves to hold the test strip, in the case of a measurement by an apparatus such as by reflection photometry, at an exactly predetermined position in the apparatus. This can for example be achieved in that for example a pin extends into the positioning hole (13) and in this manner fixes the test carrier (1) at a predetermined position.

FIG. 6 shows the underside of the test strip according to the invention containing the positioning hole (13) placed in the support (2) and the differently shaped observation openings (14 and 15) through which the detection layers can be inspected and measured.

In a diagnostic test carrier according to the invention materials which come into particular consideration for the support layer are those which do not take up the liquids to be examined. These are so-called non-absorbent materials of which plastic foils for example made of polystyrene, polyvinyl chloride, polyester, polycarbonate or polyamide are particularly preferred. However, it is also possible to impregnate absorbent materials such as wood, paper or cardboard with water-repellent agents or to coat them with a water-resistant film where silicone or hardened fats can be used as hydrophobizing agents and for example nitrocellulose or cellulose acetate can be used as film formers. Metal foils or glass are suitable as additional support materials.

In contrast for a detection layer it is necessary to use materials which are able to take up the liquid to be examined together with the components contained therein. These are so-called absorbent materials such as fleeces, fabrics, knitted fabrics, membranes or other porous plastic materials or swellable materials such as gelatin or dispersion films which can be used as layer materials. Materials which can be used for the detection layer must of course also be able to carry reagents that are necessary to detect the analyte to be determined. In the simplest case all reagents required for the detection of the analyte are on or in one layer. However, cases are also conceivable where it is more advantageous to divide the reagents over several absorbent or swellable material layers which can then be arranged above one another and in whole area contact. The term "detection layer" used in the following is intended to encompass those cases in which the reagents are either located only in or on one layer or in two or even several layers as described above.

Preferred materials for the detection layer are papers or porous plastic materials such as membranes. Of these asymmetric porous membranes are particularly preferred which are preferably arranged such that the sample liquid to be examined is applied to the large-pored side of the membrane and the analyte is determined on the fine-pored side of the membrane. Particularly preferred porous membrane materials are polyamide, polyvinylidene difluoride, polyethersulfone or polysulfone membranes. Polyamide 66 membranes and hydrophilized asymmetric polysulfone membranes are outstandingly suitable. The reagents for the determination of the analyte to be detected are usually incorporated into the aforementioned materials by impregnation or are applied to one side by coating. When coating asymmetric membranes it is preferable to coat the fine-pored side. However, so-called open films also come into consideration for the detection layer as described for example in EP-B-0 016 387. For this solids in the form of fine insoluble organic or inorganic particles are added to an aqueous dispersion of film forming organic plastics and the reagents required for the detection reaction are additionally added. Suitable film formers are preferably organic plastics such as polyvinyl esters, polyvinyl acetates, polyacrylic esters, polymethacrylic acid, polyacrylamides, polyamides, polystyrene, mixed polymers for example of butadiene and styrene or of maleic acid ester and vinyl acetate and other film-forming natural or synthetic organic polymers as well as mixtures of the same in the form of aqueous dispersions. The dispersions can be spread on a base to form a uniform layer which results in a water-resistant film after drying. The dry films have a thickness of 10 µm to 500 µm, preferably of 30 to 200 µm. The film can be used together with the base as a support or it can be mounted on another support for the detection reaction. Although the reagents required for the detection reaction are normally added to the dispersion used to produce the open films, it may also be advantageous to impregnate the final film with the reagents after its production. It is also possible to preimpregnate the filling materials with the reagents. Which reagents can be used to determine a particular analyte are known to a person skilled in the art. This does not have to be elucidated in more detail here.

An additional example of a preferred detection layer according to the invention is a film layer as described in WO-A-92 15 879. This layer is producer from a dispersion or emulsion of a polymeric film former which additionally contains a pigment, a swelling agent and the detection reagent in a homogeneous dispersion. Polyvinyl esters, polyvinyl acetates, polyacrylic esters, polymethacrylic acid, polyvinyl amides, polyamides and polystyrene are particularly suitable as polymeric film formers. In addition to homopolymers mixed polymers e.g. of butadiene, styrene or maleic acid ester are also suitable. Titanium dioxide is a particularly suitable pigment for the film. The swelling agent used should have particularly good swelling properties and methyl-vinyl ether maleic acid copolymer is particularly recommended. It is left to a person skilled in the art to decide which reagent to use to determine a particular analyte.

In a diagnostic test carrier according to the invention it is particularly preferable to use a test field as a detection layer which is composed of two layers. This test field comprises a transparent foil on which a first and a second film layer are applied on top of each other in this order. It is essential that the first layer located on the transparent foil scatters light considerably less in a wet state than the overlying second layer. The non-coated side of the transparent foil is referred to as the detection side and the side of the second layer which is opposite to the side of the second layer which lies on top of the first is referred to as the sample application side.

The film layers are produced from dispersions or emulsions of polymeric film formers. Dispersion film formers contain microscopic polymer particles which are insoluble in the carrier liquid (usually water) and which are dispersed in a very fine dispersion in the carrier liquid. If the liquid is removed by evaporation during film formation the particles approach one another and finely touch. The large forces which occur in this process and a gain in surface energy which accompanies the film formation results in growth of the particles to form a substantially closed film layer. Alternatively it is also possible to use an emulsion of a film former in which this is dissolved in a solvent. The dissolved polymer is emulsified in a carrier liquid which is immiscible with the solvent.

Polyvinyl esters, polyvinyl acetates, polyacrylic esters, polymethacrylic acid, polyvinyl amides, polyamides and polystyrene are particularly suitable as polymeric film formers. In addition to homopolymers mixed polymers e.g. of butadiene, styrene or maleic acid ester are also suitable.

In the test field the two said film layers are located on a transparent foil. Plastic foils which come especially into consideration for this are those which are liquid impermeable. Polycarbonate foil has proven to be particularly preferred.

The two film layers can be produced as coating compounds which contain the same polymeric film former or they can be produced from coating compounds which contain different polymeric film formers.

If there are special test functions and/or test conditions such as in the determination of glucose in whole blood, it is expedient to form the layers such that, apart from a good erythrocyte separation, they also have optical features which facilitate the observation of the detection reaction and the exactness of the assessment and improve the measurement.

For this the first layer expediently contains a swelling agent and optionally a weak light-scattering filling material, the second layer contains a swelling agent and at least one strongly light-scattering pigment. In addition the second layer can also contain non-porous filling materials and porous filling materials such as kieselguhr in low amounts without becoming permeable for erythrocytes.

By adding a good swelling agent (i.e. a substance which increases its volume by uptake of water) one not only obtains layers which are relatively rapidly penetrated by sample liquid but which, despite this opening effect of the swelling agent, have good erythrocyte and additionally also blood pigment separation properties. The swelling properties should be so good that for a test for which the rate of colour formation—such as for example a glucose detection reaction—largely depends on the penetration of the sample liquid through the layer, the optically detectable reaction is measurable after a maximum of one minute. Xanthan gum and methyl vinyl ether maleic acid copolymers have proven to be particularly suitable swelling agents.

Kieselguhr is also referred to as diatomaceous earth. These are deposits formed from the silicic acid skeletons of diatom species which are mined at various sites. The preferably used kieselguhr has an average particle diameter of 5-15 µm and these values were determined with a laser granulometer type 715 which is distributed by the Pabisch Company, Munich, Germany.

The amount of the strongly light-scattering pigment of the second layer is at least 25% by weight relative to the dry and ready-to-use double layer of the test field. Since the weakly light-scattering filling materials and the strongly light-scattering pigments are mainly responsible for the optical properties of the film layers, the first and the second film layer have different filling materials and pigments.

The first film layer should either contain no fillers or fillers whose refractive index is close to the refractive index of water. Precipitated silicic acids, silicon dioxide, silicates and aluminium silicate have proven to be particularly suitable for this. A sodium aluminium silicate with the trade name Transpafill® is particularly preferred.

The second layer should scatter light as strongly as possible. Ideally the refractive index of the pigments in the second film layer should be at least 2.5. Therefore titanium dioxide is preferably used. Particles with an average diameter of about 0.2 to 0.8 µm have proven to be particularly advantageous. Readily processible titanium dioxide types in the anatase modification are quite especially preferred.

Reagent systems for the detection of particular analytes by colour formation are known to a person skilled in the art. It is possible that all components of the reagent system are located in one film layer. It is, however, also possible that the components of the reagent system are divided between the two film layers. Advantageously the colour forming reagent system is at least partly located in the first film layer.

Colour formation is understood in the scope of the present invention not only to mean the transition from white to coloured but also any colour change whereby of course those colour changes are particularly preferred which are associated with the largest possible shift of the maximum absorption wavelength ($\lambda$ max).

In order to optimize the test field in the diagnostic test carrier according to the invention it has proven to be particularly advantageous when both film layers contain a non-haemolyzing wetting agent. Neutral i.e. non-charged wetting agents are particularly suitable for this. N-Octanoyl-N-methyl-glucamide is quite especially preferred. Additionally other wetting agents can be contained in the film layers which promote the homogeneity of the coatings such as sodium N-methyl-N-oleoyl-taurate.

In order to produce a test field of a diagnostic test carrier according to the invention the respective film layers are each produced successively from a homogenous dispersion of the said components. For this the transparent foil is used as a base to shape the coating compound for the first film layer. After the coating compound for the first film layer has been applied with a certain layer thickness, the layer is cried. Afterwards the coating compound for the second layer is also applied in a thin coating layer and dried. After drying the thickness of the first and second film layer should be together no more than 0.2 mm, preferably no more than 0.12 mm and particularly preferably no more than 0.08 mm.

The attachment can be carried out by methods known to a person skilled in the art from test carrier technology. For example the attachment can be by means of hot-melt adhesive or hardening cold-setting adhesive. In this connection a spotted or rastered glueing is advantageous since this especially facilitates capillary active liquid transport. Double-sided adhesive strips have also proven to be advantageous. However, in all cases it is important that the attachment of the overlay on the support layer is such that a capillary-active liquid transport is possible from the detection layer into that part of the overlay which is attached to the support layer. This capillary-active liquid transport must be especially possible when the detection layer is saturated with liquid. Adhesive tapes containing natural or synthetic rubber have proven to be particularly suitable for the manufacture. It is particularly advantageous when the agent that is used to attach the overlay to the support layer has approximately the same thickness as the detection layer(s). It then serves as a spacer in order to keep the entire overlay according to the invention level on a continuous plane even outside the region of the detection layer(s).

In order to determine the analyte to be detected in the sample liquid, the detection layer but at least the reaction zones thereof i.e. the regions of the detection layer(s) which carry reagent which can be observed for signal formation and measured, are visible through the support layer in the diagnostic test carrier according to the invention. As already described above this can be achieved by having a transparent support layer. It is, however, also possible that the support layer has a perforation which is covered by the detection layer or the detection layers. The detection layer or the detection layers but at least the reaction zones of the detection layers are then visible through the perforation. In a preferred embodiment of the diagnostic test carrier according to the invention there is a hole in the support layer below the detection layer through which the detection layer or a reaction zone can be observed. The hole has a somewhat smaller diameter than the smallest linear extension of the detection layer so that the detection layer rests on the support layer outside the hole and can be attached there. Advantageously the detection layer is adequately attached by double-sided adhesive tapes arranged on both sides and by the overlay according to the invention lying over the detection layer and its attachment to the support layer. However, the detection layer itself is also preferably attached to the support layer by at least a thin adhesive tape.

It is, however, also possible to observe several reaction zones of a detection layer through a hole.

The perforation of a diagnostic test carrier according to the invention can also be composed of two or several holes which can be used to determine the analyte (one or several analytes). Various detection layers or only one detection layer with several reaction zones can be arranged above the holes so that through each hole one detection layer or one reaction zone can be observed. It is, however, also possible that several reaction zones can be observed through one hole.

An inert cover made of sample-impermeable, usually water-impermeable and non-absorbent material can be arranged over the spreading overlay according to the invention of the diagnostic test carrier according to the invention in such a manner that it covers the region of the overlay outside the detection layer. Ideally the cover also extends into the region of the detection layer but, however, in any case leaves a middle part of the overlay according to the invention which covers the detection layer free. This free part of the overlay is referred to as the sample application site.

Plastic foils have proven to be particularly advantageous as a cover. If the cover and the overlay according to the invention have different colours, for example white and yellow or white and red, then this clearly indicates the site at which the sample liquid to be examined should be applied.

The direction i.e. which end of a diagnostic test carrier according to the invention should be placed or inserted into a measuring instrument can also be made evident on the cover for example by printing on one or several arrows.

A sample application site can particularly simply be prepared by a cover of two strip-shaped plastic foils which leave a strip-like region of the overlay according to the invention covering the detection layer free. If 2 or more sample application sites are intended then three or more strip-shaped plastic foils have to be used. The foils used for the cover are attached to the overlay according to the invention and optionally to the support layer. Hot-melt adhesives which are preferably applied in spots or in a pattern on the support layer or on the underside of the cover are suitable for such an attachment or adhesive tapes if the foils are not self-adhesive. The sample application site is preferably located above the perforation in the support layer through which a signal generation on the detection layer can be observed.

In order to carry out a method for the determination of an analyte in a liquid sample with the aid of a diagnostic test carrier according to the invention the sample liquid is applied to the side of the overlay which faces away from the detection layer and ideally sufficient so that the liquid which passes through the overlay according to the invention completely saturates the detection layer. Body fluids such as blood, plasma, serum, urine, saliva etc. come into particular consideration as the sample liquid. Blood or liquids derived from blood such as plasma or serum and urine are particularly preferred sample liquids. Then if the analyte to be determined is present a signal can be detected in the detection layer. Such a signal is advantageously a colour change which is understood as colour formation, loss of colour as well as colour transition. The intensity of the colour change is a measure for the amount of analyte in the examined liquid sample. It can be evaluated visually or quantitatively with the aid of an instrument, usually by reflection photometry, in which case calibration curves created in preliminary experiments can be used. Alternatively the content of analyte can be displayed directly by means of the instrument's software.

A major advantage of the diagnostic test carrier according to the invention is that it is not necessary to apply a predetermined volume of a sample liquid on the test carrier.

It has namely turned out that when a test strip is used which has been constructed using the above-mentioned preferred materials, a sample excess is not taken up by the strip but rather remains above the application site. A further major advantage of the constructions according to the invention is that the test strip is self-dosing. If its application site is brought into contact with a blood drop standing on or hanging from the finger pad the strip only takes up the amount that is required to saturate the detection layer(s), the remainder remains on the finger.

In this manner the signal intensity which develops when an analyte is present is independent of the amount and the duration of contact between sample liquid and detection layer. The colour which has developed after completion of the detection reaction which is usually within a few seconds to a few minutes thus remains unchanged for the measurement. It is only determined by the stability of the colour generating system. False-positive results are thus also avoided and a quantitative analyte determination is possible.

Covering parts of the overlay according to the invention and thus marking the sample application site ensures that liquid can only reach the detection layer at the optimal site for this. In combination with a detection layer that only takes up a small amount of liquid and nevertheless ensures an intensive signal generation, this ensures that reliable analyte determinations are possible even with very small sample volumes. Since the test carrier according to the invention is only composed of a few components which can be simply and rapidly assembled, it is very cheap to manufacture.

The following application examples illustrate the manufacture of spreading layers according to the invention and their use.

EXAMPLE 1

A.) Production of a Spreading Overlay According to the Invention

A.1) 55.0 g N-oleoyl-sarcosine ("®Crodasinic O" from the Croda Company, Nettetal, Germany) is added to 55 kg distilled water and adjusted to pH 6.0 while stirring by adding 11.0 g 32% by weight sodium hydroxide solution. A wetting solution which can be used according to the invention is obtained containing ca. 0.106% by weight active substance.

A.2) A 1 m wide, 700 m long ®Viledon fleece, type FO2451/121 from the Freudenberg Company, Weinheim, Germany (thickness 50 μm, weight per unit area 18 g/m²) is pulled through this solution at a speed of 5 m/min. The impregnated fleece is subsequently dried in a horizontal drier of 30 m length at 80° C. and at an air throughput of 50 m³/min. The liquor pick-up of the fleece was 45 ml/m² so that the content of active substance on the impregnated fleece is ca. 0.26% by weight.

B.) Manufacture of Test Strips According to the Invention

B.1) A 5 mm wide double-sided adhesive tape (polyester support and synthetic rubber adhesive) is mounted parallel on a strip-shaped 50 mm wide titanium dioxide-containing polyester support layer at a distance of 18.6 mm to its left edge (measured from the left edge of the adhesive tape). Two holes are punched out of this sandwich at a distance of 6 mm i.e. a positioning hole and an inspection and measuring hole whose centres lie on a straight line perpendicular to the longitudinal axis of the carrier strip. The first hole, the positioning hole, is circular, has a diameter of 2.6 mm and its centre is at a distance of 4 mm from the left edge of the carrier strip. The second hole is also round with a diameter of 4 mm. The centre of the second hole is at a distance of 21 mm from the left edge of the carrier strip.

Afterwards the protective paper on the double-sided adhesive tape is pulled off.

The procedure for the production of a detection layer which is composed of 2 film layers is as follows:

B.2) The following components are added together in a beaker as pure substances or in the form of stock solutions in the following composition and mixed by stirring:
water: 820.0 g
citric acid-1 hydrate: 2.5 g
calcium chloride-2-hydrate: 0.5 g
sodium hydroxide: 1.4 g
xanthan gum: 3.4 g
tetraethylammonium chloride: 2.0 g
sodium N-methyl-N-olecyl-taurate: 0.29 g
N-octanoyl-N-methylglucamide: 2.1 g
polyvinylpyrrolidone (MW 25000): 3.5 g
Transpafill (sodium-aluminium silicate): 62.1 g
polyvinylpropionate dispersion (50% by weight in water): 60.8 g
Bis-(2-hydroxyethyl)-(4-hydroxyiminocyclohexa-2,5-dienylidine)-ammonium chloride: 1.2 g
2,18-phosphomolybdic acid hexasodium salt: 16.1 g
pyrroloquinolin<quinone: 32 mg
glucose dehydrogenase rec. from Acinetobacter calcoaceticus, 1.7 MU EC 1.1.99.17: (2.4 g)
1-hexanol: 1.6 g
1-methoxy-2-propanol: 20.4 g
The total composition is adjusted with NAOH to a pH of ca. 6 and then coated on a 125 μm thick polycarbonate foil at a weight per unit area of 89 g/m² and dried.

B.3) The following components are added together in a beaker as pure substances or in the form of stock solutions in the following composition and mixed by stirring:
Water: 579.7 g
sodium hydroxide: 3.4 g
Gantrez (methyl vinyl ether maleic acid copolymer): 13.8 g
sodium N-methyl-N-oleoyl-taurate 0.25 g
N-octanoyl-N-methyl-glucamide: 3.6 g
tetraethylammonium chloride: 9.7 g
polyvinylpyrrolidone (MW 25000): 20.2 g
titanium dioxide: 177.1 g
kieselguhr: 55.3 g
polyvinylpropionate dispersion (50% weight in water): 70.6 g 2,18-phosphomolybdic acid hexasodium salt: 44.3 g
potassium hexacyanoferrate (III): 0.3 g
1-hexanol: 1.6 g
1-methoxy-2-propanol: 20.4 g
The total composition is adjusted with NaOH to a pH of ca. 6 and then coated on a polycarbonate foil as described under A. at a weight per unit area of 104 g/m² and dried.

B.4) A 5 mm wide strip of the detection layer produced in this way is fitted accurately and glued onto the foil side of the perforated double-sided adhesive tape on the support layer.

Double single-sided adhesive tapes (PVC support and natural rubber adhesive) are glued as spacers onto the carrier foil directly adjacent to and on both sides of the detection layer. In the present example one spacer is 6 mm and the other 9 mm wide. Afterwards the protective foil of the two double-sided adhesive tapes is pulled off.

A 20 mm wide strip of the spreading fleece produced in section A is placed on this composite and glued by pressing.

Two single-sided adhesive tapes (PVC support and natural rubber adhesive) are glued as covers onto the spreading fleece in such a way that the spacers are completely covered and there is at least a slight overlap with the reactive zone. The tapeware is thus finished.

The tapeware is cut into 6 mm wide test carriers such that the measuring hole lies in the middle of the test carrier.

EXAMPLE 2

Manufacture of a diagnostic test carrier according to the invention containing two detection fields for the determination of glucose at a low and high concentration.

The test carrier is manufactured according to FIGS. 4, 5 and 6 with the following process steps:

A 10 mm wide double-sided adhesive tape (polyester support and synthetic rubber adhesive) is mounted parallel on a strip-shaped 50 mm wide titanium dioxide-containing polyester support layer at a distance of 18.6 mm to its left edge (measured from the left edge of the adhesive tape). Three holes are punched out of this sandwich at a distance of 6 mm i.e. a positioning hole and two inspection and measuring holes whose centres lie on a straight line perpendicular to the longitudinal axis of the carrier strip. The first hole, the positioning hole, is circular, has a diameter of 2.6 mm and its centre is at a distance of 4 mm from the left edge of the carrier strip. The second hole is also round with a diameter of 4 mm, the third hole is rectangular with an edge length of 3 mm in the longitudinal direction of the strip and 4 mm in the cross direction. Both the second and third hole have a centre to centre distance of 5.1 mm on the adhesive tape, the centre of the second hole is at a distance of 21 mm from the left edge of the carrier strip.

Afterwards the protective paper on the double-sided adhesive tape is pulled off.

The procedure for the production of the first detection layer which is composed of 2 film layers is as follows:

A. The following components are added together in a beaker as pure substances or in the form of stock solutions in the following composition and mixed by stirring:
water: 820.0 g
citric acid-1 hydrate: 2.5 g
calcium chloride-2-hydrate: 0.5 g
sodium hydroxide: 1.4 g
xanthan gum: 3.4 g
tetraethylammonium chloride: 2.0 g
N-octanoyl-N-methylglucamide: 2.1 g
sodium N-methyl-N-oleoyl-taurate: 0.29 g polyvinylpyrrolidone (MW 25000): 3.5 g
Transpafill (sodium-aluminium silicate): 62.1 g
polyvinylpropionate dispersion (50% by weight in water): 60.8 g
Bis-(2-hydroxyethyl)-(4-hydroxyiminocyclohexa-2,5-dienylidine)-ammonium chloride: 1.2 g
2,18-phosphomolybdic acid hexasodium salt: 16.1 g
pyrroloquinoline quinone: 32 mg
glucose dehydrogenase rec. from Acinetobacter calcoaceticus, 1.7 MU EC 1.1.99.17: (2.4 g)
1-hexanol: 1.6 g
1-methoxy-2-propanol: 20.4 g The total composition is adjusted with NaOH to a pH of ca. 6 and then coated on a 125 μ thick polycarbonate foil at a weight per unit area of 89 g/m² and dried.

B. The following components are added together in a beaker as pure substances or in the form of stock solutions in the following composition and mixed by stirring:
Water: 579.7 g
sodium hydroxide: 3.4 g
Gantrez (methyl vinyl ether maleic acid copolymer): 13.8 g
N-octanoyl-N-methyl-glucamide: 3.6 g
tetraethylammonium chloride: 9.7 g
polyvinylpyrrolidone (MW 25000): 20.2 g
titanium dioxide: 177.1 g
kieselguhr: 55.3 g
polyvinylpropionate dispersion (50% weight in water): 70.6 g
2,18-phosphomolybdic acid hexasodium salt: 44.3 g
potassium hexacyanoferrate (III): 0.3 g
1-hexanol: 1.6 g
1-methoxy-2-propanol: 20.4 g The total composition is adjusted with NaOH to a pH of ca. 6 and then coated on the polycarbonate foil described under A. at a weight per unit area of 104 g/m² and dried. After drying the layer thickness is 60 μm.

The second detection layer which is also composed of 2 film layers is manufactured as follows:

A. The following components are added together in a beaker as pure substances or in the form of stock solutions in the stated amounts and mixed by stirring:
water: 820.0 g
citric acid-1 hydrate: 2.5 g
calcium chloride-2-hydrate: 0.5 g
sodium hydroxide: 1.4 g
xanthan gum: 3.4 g
tetraethylammonium chloride: 4.22 g
N-octanoyl-N-methylglucamide: 2.1 g
sodium N-methyl-N-oleoyl-taurate: 0.29 g
polyvinylpyrrolidone (MW 25000): 3.5 g
Transpafill (sodium-aluminium silicate): 62.1 g
polyvinylpropionate dispersion (50% by weight in water): 60.8 g
N-(4-nitrosophenyl)-N'-carboxymethyl-piperazine: 1.0 g
2,18-phosphomolybdic acid hexasodium salt: 20.9 g
pyrroloquinoline quinone: 32 mg
glucose dehydrogenase rec. from Acinetobacter calcoaceticus, 1.7 MU EC 1.1.99.17: (2.4 g)
1-hexanol: 1.6 g
1-methoxy-2-propanol: 20.4 g The total composition is adjusted with NaOH to a pH of ca. 6 and then coated on a 125 μm thick polycarbonate foil at a weight per unit area of 89 g/m² and dried.

B. The following components are added together in a beaker as pure substances or in the form of stock solutions in the stated amounts and mixed by stirring:
Water: 579.7 g
sodium hydroxide: 3.4 g
Gantrez (methyl vinyl ether maleic acid copolymer): 13.8 g
tetraethylammonium chloride: 6.71 g
N-octanoyl-N-methyl-glucamide: 2.74 g
sodium N-methyl-N-oleoyl-taurate 0.25 g
polyvinylpyrrolidone (MW 25000): 15.6 g
titanium dioxide: 136.7 g
polyvinylpropionate dispersion (50% weight in water): 54.6 g
N-(4-nitrosophenyl)-N'-carboxymethyl piperazine: 1.51 g
2,18-phosphomolybdic acid hexasodium salt: 33.13 g
potassium hexacyanoferrate (III): 0.28 g
1-hexanol: 1.6 g
1-methoxy-2-propanol: 20.4 g The total composition is adjusted with NaOH to a pH of ca. 6 and then coated on the polycarbonate foil described under A. at a weight per unit area of 102 g/m² and dried. After drying the layer thickness is 55 μm.

The foil side of a 5 mm wide strip of each of the detection layers prepared in this manner is glued and fitted accurately on the support layer on the punched double-sided adhesive tape in such a manner that the strips are directly adjacent to one another.

Double-sided adhesive tapes having the thickness of the detection strips (PVC support and natural rubber adhesive) are glued as spacers onto the carrier foil directly adjacent to and on both sides of the detection layers. In the present example one spacer is 6 mm and the other is 9 mm wide. Afterwards the protective foil of the two double-sided adhesive tapes is pulled off.

Then a 10 mm wide strip of a spreading fleece manufactured according to section A in example 1 is placed on the 9 mm wide spacer in such a manner that the cut edge of the fabric strip overhangs the borderline between the detection strips by 0.5 to 0.6 mm and is fixed by pressing. Subsequently a 10 mm wide strip of the same spreading fleece according to the invention is placed on the 6 mm wide spacer in such a manner that it overlaps the cut edge of the first fabric strip by 1 to 1.2 mm and is fixed by pressing.

Afterwards two single-sided adhesive tapes (PVC support and natural rubber adhesive) are glued as covers onto both sides of the construction in such a manner that a gap of 2 to 2.5 mm remains uncovered symmetrical to the borderline of the detection strips. The tapeware is thus finished.

The tapeware is cut into 6 mm wide test carriers such that the measuring and inspection holes and the positioning hole lie in the middle of the test carrier.

EXAMPLE 3

Test strips are manufactured according to example 2 which have the same detection layers in both detection fields. A polyester fabric type PE 38 HC impregnated with 0.25% by weight sodium N-oleoyl-sarcosinate is used as a spreading layer. The strips are inserted into a GLU-COTREND instrument set up to measure both test fields simultaneously during which they are subjected to a slight bending in order to fix them in their measurement position.

The strips are spotted with increasing volumes of EDTA venous blood containing 102 mg/dl glucose. For each volume 5 series of 10 test strips were measured (n=5, N=50). From this 5 CV values were calculated for each volume. (The CV value is defined as the relative standard deviation CV=standard deviation/mean and is stated in %).

The following table shows the medians of the measured results and the medians of the CV values of the 5 series per volume:

|  | Field 1 | | Field 2 | |
| --- | --- | --- | --- | --- |
| Volume | median of the measured value [mg/dl] | median of the CV value [%] | median of the measured value [mg/dl] | median of the CV value [%] |
| 3 µl | error* | — | 63.4** | 9.3 |
| 4 µl | 100 | 2.5 | 102 | 2.7 |
| 5 µl | 102 | 2.3 | 103 | 2.6 |
| 10 µl | 101 | 2.2 | 102 | 2.7 |
| 15 µl | 103 | 2.4 | 102 | 2.7 |

Remarks:
*An inhomogeneous reaction colouration on field 1 is detected by the 2-LED optics of the instrument (described in EP-A-819 943). The instrument therefore only gives an error message but no measured value.
**Field 2 is only illuminated with one LED so that an inhomogeneous colouration of the test field is not detected. Consequently the CV value is greatly increased. However, the instrument can give the error message "different intensities of the reaction colour of both fields" by comparing both test fields. This function was switched off during the measurement carried out in this case.

The experiments show that both test fields indicate the same colour i.e. the same glucose concentration above a sample volume of 4 µl. This demonstrates the excellent spreading action over both measurement fields of the overlay according to the invention. With higher sample volumes the value does not change since the excess sample material remains above the application gap. With smaller volumes the wetting and hence also the colouration of the two reaction zones is incomplete which can be detected by the 2 LED optics of field 1. Appropriate software measures can prevent such measurements from leading to a display of (false-negative) values. Instead an error message is displayed which indicates to the user that the sample volume is too low.

The invention claimed is:

1. A test strip for analyzing an analyte comprising a flexible flat support on which one or several test fields are arranged next to one another, wherein said test fields carry one or several detection layers stacked on top of one another each detection layer including a reagent which provides a signal visibly detectable through the support layer in the presence of the analyte and wherein the detection layers are directly contacted by an overlay made of a spreading material comprising a porous flat structure impregnated with a wetting agent, wherein the wetting agent is N-oleoyl-sarcosinate, wherein the overlay comprises one or several flat overlay elements which are attached to the test strip in such a way that at least a part of their surface can move freely relative to the strip surface when the test strip is bent towards a side on which the overlay is located; and further wherein the parts of said overlay elements that can "move freely relative to the strip surface" face one another and overlap.

2. The test strip of claim 1 wherein the overlap covers two test fields.

3. A test strip comprising a flexible flat support on which one or several test fields are arranged next to one another, wherein said test fields carry one or several detection layers stacked on top of one another, and wherein the test fields are covered two overlay elements whose parts overlap and which can move freely relative to the strip surface face one another when the test strip is bent towards a side on which the overlay is located, said overlay elements made of a spreading material comprising a porous flat structure impregnated with a wetting agent, wherein the wetting agent is N-oleoyl-sarcosinate.

4. The test strip of claim 3 wherein the overlap covers two test fields.

* * * * *